(12) United States Patent
Brocke et al.

(10) Patent No.: US 12,402,552 B2
(45) Date of Patent: Sep. 2, 2025

(54) METHOD FOR ASCERTAINING A SOIL CONDITION

(71) Applicant: DEERE & COMPANY, Moline, IL (US)

(72) Inventors: Stefan Brocke, Mannheim (DE); Florian Schott, Einhausen (DE)

(73) Assignee: Deere & Company, Moline, IL (US)

( * ) Notice: Subject to any disclaimer, the term of this patent is extended or adjusted under 35 U.S.C. 154(b) by 299 days.

(21) Appl. No.: 18/322,732

(22) Filed: May 24, 2023

(65) Prior Publication Data
US 2023/0380328 A1 Nov. 30, 2023

(30) Foreign Application Priority Data
May 27, 2022 (DE) .......................... 102022113393.1

(51) Int. Cl.
*A01B 79/00* (2006.01)
*G01N 33/24* (2006.01)

(52) U.S. Cl.
CPC ........... *A01B 79/005* (2013.01); *G01N 33/24* (2013.01); *G01N 33/245* (2024.05)

(58) Field of Classification Search
CPC ...... A01B 79/00; A01B 79/005; G01N 33/24; G01N 33/245
See application file for complete search history.

(56) References Cited

U.S. PATENT DOCUMENTS

| | | | |
|---|---|---|---|
| 9,668,399 B2* | 6/2017 | Gates | A01B 63/245 |
| 10,820,474 B2* | 11/2020 | Pomedli | G01N 21/84 |
| 11,131,076 B2 | 9/2021 | Cherney et al. | |
| 11,175,254 B2* | 11/2021 | Puhalla | A01B 47/00 |
| 2018/0265145 A1 | 9/2018 | Todd et al. | |
| 2020/0260633 A1* | 8/2020 | Kovach | A01B 71/02 |
| 2021/0173399 A1 | 6/2021 | Richard et al. | |
| 2021/0237570 A1 | 8/2021 | Kremmer et al. | |
| 2021/0362705 A1* | 11/2021 | Singh | A01B 69/008 |
| 2021/0388575 A1 | 12/2021 | Cherney et al. | |
| 2022/0163436 A1* | 5/2022 | López-Cuervo Medina | A01B 79/005 |
| 2024/0206363 A1* | 6/2024 | Kowalchuk | A01B 79/005 |
| 2025/0085712 A1* | 3/2025 | Horeth | B60W 60/00182 |

OTHER PUBLICATIONS

European Search Report issued in Application No. 23171619.2, dated Oct. 27, 2023, 7 pages.

* cited by examiner

*Primary Examiner* — Nguyen Q. Ha

(57) ABSTRACT

A method for ascertaining a soil condition includes observing via a detection device, including a sensor, a kinematic behavior of a track drive caused by sinking when driving on a compressible underlying surface, and determining via an assessment device, including a processor connected to memory, at least one parameter characterizing the soil condition based in part on the observed kinematic behavior of the track drive.

20 Claims, 2 Drawing Sheets

METHOD FOR ASCERTAINING A SOIL CONDITION

CROSS-REFERENCE TO RELATED APPLICATIONS

This application claims priority to German Patent Application No. 102022113393.1, filed May 27, 2022, which is hereby incorporated by reference.

FIELD OF THE DISCLOSURE

The disclosure relates to a method for ascertaining a soil condition.

BACKGROUND

Work machines with track drives traverse a variety of ground surfaces.

SUMMARY

The knowledge about the soil condition of a field surface to be treated is needed for the correct application of agricultural treatment methods or techniques. This is reflected, inter alia, in the selection of suitable soil treatment devices or working parameters, for example, defining the treatment depth of soil-engaging work tools on a plow, a cultivator, a seed drill, or the like, and with respect to the question of a tire filling pressure to be selected, an optimum sowing or harvesting time, or the efficient and environmentally protective weed control.

The soil condition is characterized in this case, inter alia, by the soil structure, soil organisms (biological activity), the moisture content, and the degree of compaction of the soil surface. In the normal case, an assessment is carried out visually by the agricultural user, which presumes corresponding experience, or else on the basis of soil measurements carried out as random samples via stationary or mobile analysis devices.

In view of this, it is an object of the present disclosure to specify a method of the type mentioned in the outset such that continuous provision of items of information relating to the soil condition of a field surface to be treated is enabled.

This object is achieved by a method for ascertaining a soil condition having the features of one or more of the following embodiments.

The method according to the disclosure for ascertaining a soil condition provides that a kinematic behavior of a track drive caused by sinking when driving on a compressible underlying surface is observed via a detection device, wherein at least one parameter characterizing the soil condition is concluded by an assessment device starting from the observed kinematic behavior of the track drive.

This procedure makes use of the circumstance that with increasing demands for the protection of the soil, agricultural and forestry work machines or work devices are increasingly being equipped with track drives. These typically comprise a drive belt produced from fiber-reinforced rubber, which is guided on a chassis via a plurality of driven or freely rotating deflection, tensioning, and support rollers. Depending on the complexity of the chassis, at least a part of the rollers is suspended in an articulated or sprung manner such that the course of the drive belt can adapt itself to the irregularities of the underlying surface driven on. The type of the articulation or spring suspension of the rollers has significant influence in this case on the pressure distribution between drive belt and underlying surface, wherein this is usually asymmetrical under the effect of the drive torques occurring on the drive belt. Each track drive type or each track drive model insofar has a specific or characteristic signature with respect to its compression effect on the underlying surface respectively driven on. In this way, it is possible during the travel operation of a work machine equipped with a track drive or a work device equipped therewith by acquiring the kinematic behavior of the track drive observed as it sinks into the underlying surface to continuously conclude the soil condition or the parameters representative thereof. For this purpose, the kinematic behavior observed via the detection device is supplied to a prediction model predetermined for the relevant track drive, on the basis of which a statement is in turn made with respect to the soil condition.

Since the compression effect caused by the respective track drive is also dependent on the scope of the traction torque occurring on the drive belt in relation to the underlying surface because of drive and/or the axle load acting in a linkage point of the track drive in relation to a vehicle chassis because of weight, furthermore corresponding items of information of a drive system and/or an axle load sensor can be considered to improve the accuracy of the prediction model, in order to take into consideration the above-mentioned influences.

The prediction model is trained beforehand on the basis of empirically performed test and measurement series and uploaded into a processor unit provided for executing the method according to the disclosure, which is part of the assessment device. The prediction model establishes a clear correlation between the observed kinematic behavior of the track drive and the respective soil condition. Moreover, the use of corresponding AI methods (AI—artificial intelligence) suggests itself to improve the prediction horizon.

The work machine can be an agricultural tractor, a harvesting machine, or a forestry work vehicle. In addition, the use of the method according to the disclosure is also conceivable in agricultural or forestry work devices, such as driven cargo trailers or the like.

Advantageous embodiments of the method are disclosed herein.

The kinematic behavior can result on the basis of a deflection which occurs because of travel on a chassis component of the track drive mounted so it is movable in relation to the underlying surface. In one example, the chassis is attached via a base part via a pivot joint in a pivotable manner on a vehicle chassis, so that the deflection to be observed results from an angle change around the pivot joint axis sensorially detectable via the detection device. A traction torque occurring on the drive belt because of drive in relation to the underlying surface causes asymmetrical sinking of the track drive counter to the travel direction, which is expressed in a corresponding angle change.

As already mentioned, in complex drive arrangements, further movable chassis components can also be provided, which are used for the spring suspension and/or the tensioning of the drive belt via associated deflection, tensioning, and support rollers. A complex and therefore particularly distinctive deflection pattern results from the comprehensive sensorial detection of the movements insofar occurring, which permits an accurate inference of the respective soil condition.

Furthermore, it is possible that the kinematic behavior results due to a normal and/or tangential acceleration, which occurs because of travel on a section of the drive belt facing toward the underlying surface. The knowledge of the normal and/or tangential acceleration can be used by the assessment device to ascertain the orientation of the relevant belt section in relation to the underlying surface. This procedure is substantially independent of the specific structural design of the chassis and can be used redundantly for the deflection-based assessment of the kinematic behavior of the track drive.

The normal and/or tangential acceleration can be determined via an acceleration sensor embedded in the belt section as part of the detection device, wherein a data stream representing this is transmitted wirelessly to the assessment device. The acceleration sensor can be housed protected from mechanical influences on an inside of the drive belt or embedded therein. For this purpose, the acceleration sensor and a radio interface provided for data transfer can be provided with electrical energy from an installed accumulator, which may be externally charged inductively and thus contactlessly, or a generator that generates power under the movement of the drive belt. Acceleration sensor, radio interface, and accumulator or power-generating generator are integrated, for example, in a common acceleration measurement module.

The vehicle chassis is typically used as a reference system for ascertaining the orientation of the belt section. For this purpose, a separate acceleration sensor for determining a reference orientation is assigned thereto.

Since the drive belt is deflected multiple times along its course, it is conceivable for uninterrupted detection of the normal and/or tangential acceleration to arrange in a distributed manner a number of acceleration sensors corresponding to the deflection points along the drive belt.

With regard to the most accurate possible ascertainment of the soil condition, it can be provided that the observed kinematic behavior of the track drive is filtered by the assessment device with respect to soil irregularities located in the travel direction. The detection of the soil irregularities can be performed via forward-looking sensor devices for three-dimensional surroundings detection, for example, in the form of a stereo camera or a lidar.

The parameters characterizing the soil condition are typically items of information with respect to a soil moisture, a soil structure, a soil compaction, and/or a soil type. The ascertainment of the soil condition can also be restricted for this purpose to a selection of the above-mentioned parameters, wherein in particular specifications with respect to a current moisture content, therefore the soil moisture, originate from alternative data sources and can thus contribute to improved accuracy of the remaining parameters. The moisture content results, for example, from items of weather information or a soil measurement carried out on location.

In order to make the items of information obtained with regard to the soil condition usable in particular when driving on the same field surface again, it is possible that the ascertained parameters are located via a navigation system communicating with the assessment device by linking to an associated cartographic position and transmitted as a data set to a central data server. From there, these can be downloaded by a user for circuit diagram creation or process optimization.

The above and other features will become apparent from the following detailed description and accompanying drawings.

BRIEF DESCRIPTION OF THE DRAWINGS

The method according to the disclosure for ascertaining a soil condition will be described in more detail hereinafter on the basis of the drawings. Here, identical reference signs relate to corresponding components or components which are of comparable function. In the drawings.

DETAILED DESCRIPTION

The embodiments or implementations disclosed in the above drawings and the following detailed description are not intended to be exhaustive or to limit the present disclosure to these embodiments or implementations.

Figure 1:
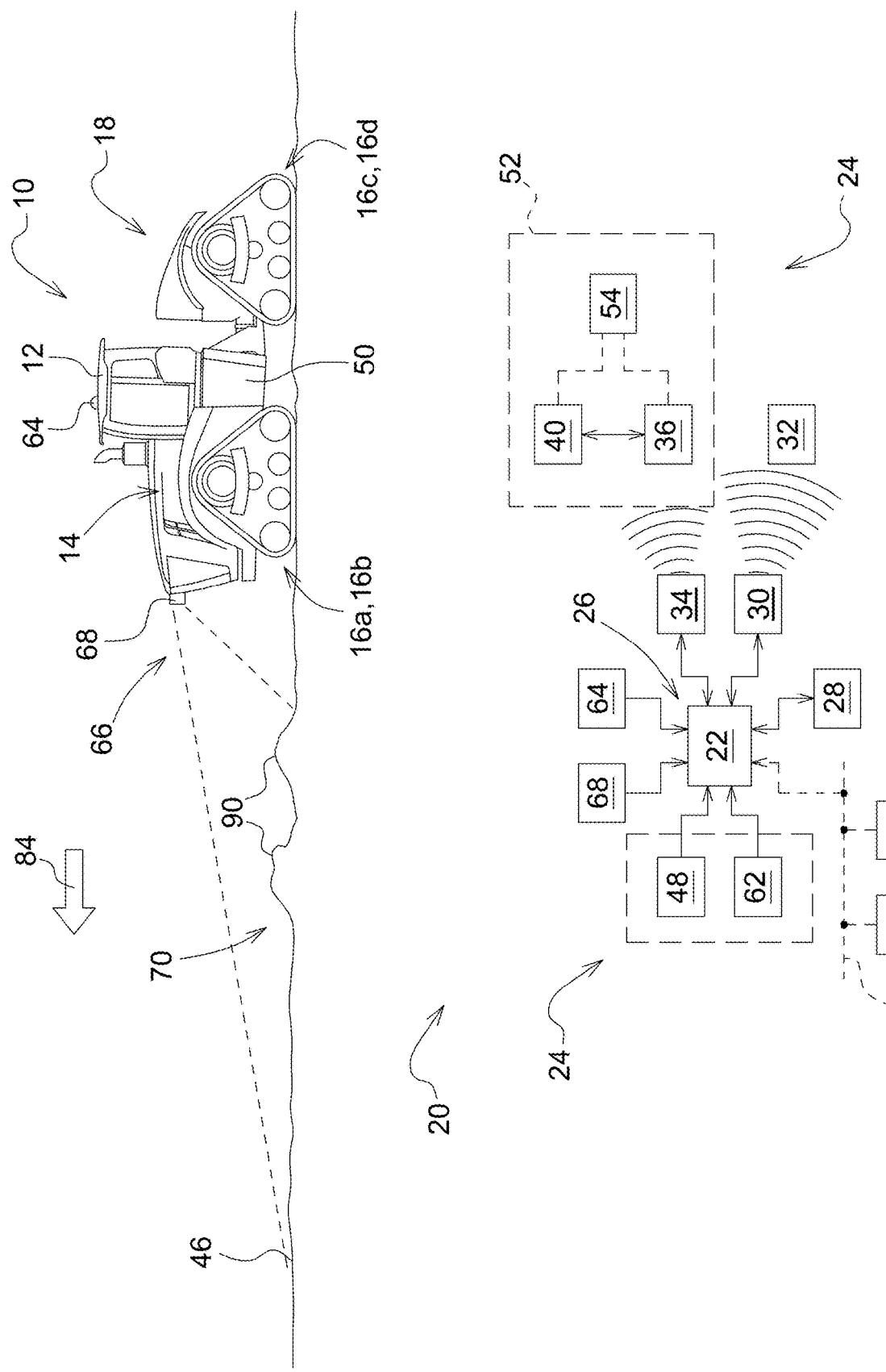
FIG. 1 shows an arrangement located in an agricultural tractor for carrying out the method according to the disclosure for ascertaining a soil condition.

FIG. 1 shows an arrangement housed in an agricultural tractor for carrying out the method according to the disclosure for ascertaining a soil condition.

The agricultural tractor 10 is in the present case an articulated four-track tractor 12, in which a front axle 14 is assigned a first pair of driven track drives 16a, 16b and a rear axle 18 is assigned a second pair of driven track drives 16c, 16d. In this case, due to the selected view, just the track drives 16a, 16c provided on the left side of the agricultural tractor 10 are visible, the track drives 16b, 16d assigned to the right side are concealed along the line of sight and are arranged in a mirror image to the two track drives 16a, 16c.

The arrangement 20 comprises a processor unit 22 (e.g., a processor), which is part of an assessment device 26 communicating with a detection device 24 and has a data exchange connection with a memory unit 28 (e.g., memory) and, via a first wireless interface 30, with a central data server 32 or, via a second wireless interface 34, with a radio interface 36 of a first acceleration sensor 40 (see FIG. 2) embedded in a drive belt 38 produced from fiber-reinforced rubber.

Figure 2:
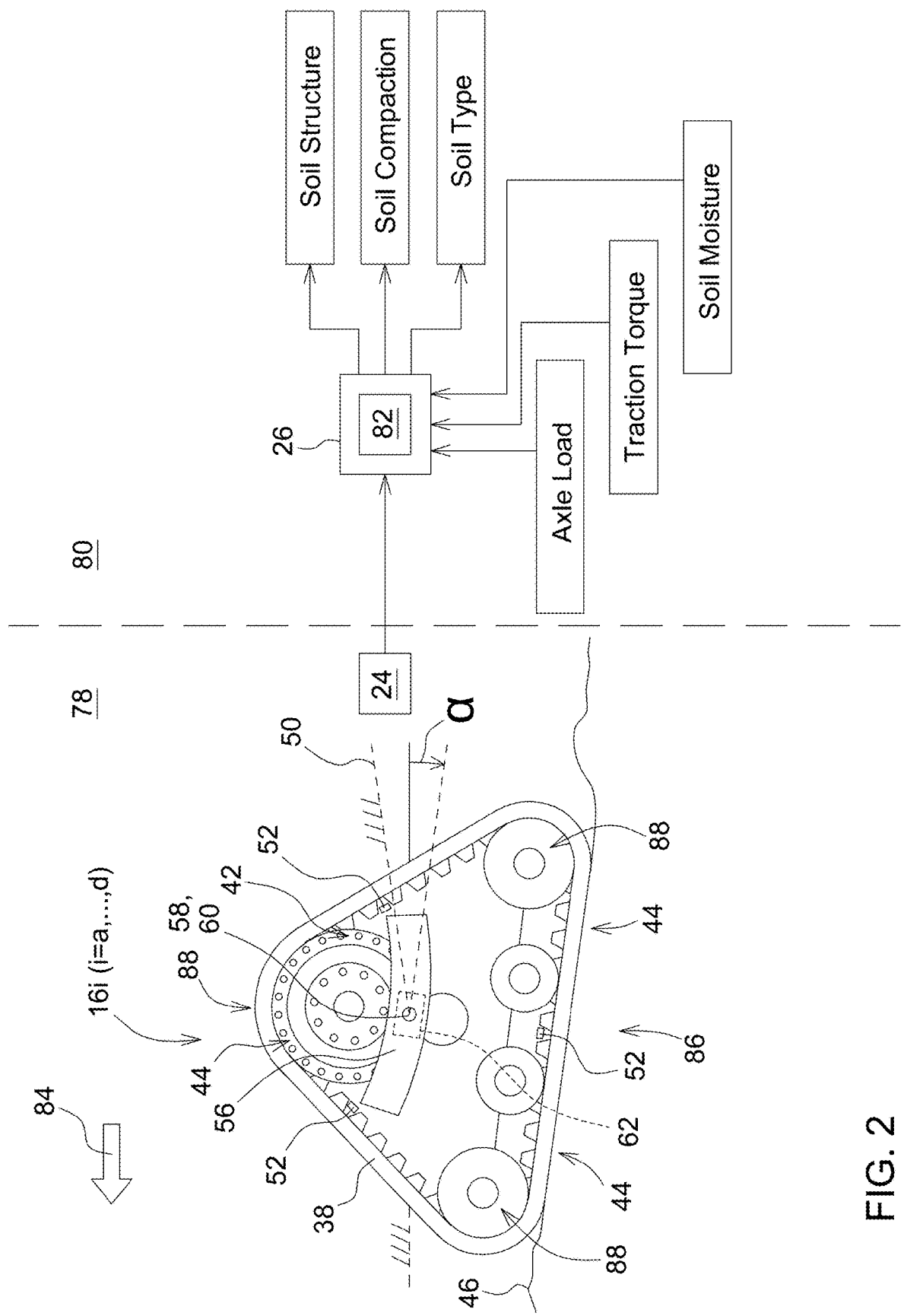
FIG. 2 shows an exemplary embodiment of the method according to the disclosure illustrated as a block diagram.

According to the illustration of a single track drive 16i (i=a, . . . , d) in FIG. 2, the drive belt 38 is guided on a chassis 42 via a plurality of driven or freely rotating deflection, tensioning, and support rollers 44. Depending on the complexity of the chassis 42, at least a part of the rollers 44 is suspended in an articulated or sprung manner in such a way that the course of the drive belt 38 can adapt itself to the irregularities of an underlying surface 46 being driven on.

In addition, a second acceleration sensor 48 connected to the processor unit 22 is provided. This is attached to a vehicle chassis 50 of the agricultural tractor 10 and is part of the detection device 24 jointly with the first acceleration sensor 40.

The first acceleration sensor 40 and the radio interface 36 are integrated in a common acceleration measurement module 52 and are supplied with electrical energy via an installed accumulator 54, which may be externally charged inductively and thus contactlessly. In this case, the acceleration measurement module 52 is embedded on an inside of the drive belt 38 protected from mechanical influences.

As can be seen best in FIG. 2, the chassis 42 of the track drive 16i is attached in a pivotable manner via a base part 56 via a pivot joint 58 on the vehicle chassis 50, wherein an angle change α occurring along a pivot joint axis 60 is sensorially detected via an incremental rotational encoder 62, which is also comprised by the detection device 24.

Furthermore, a GPS-based navigation system 64 is used to ascertain a current cartographic position of the agricultural tractor 10, wherein the respectively ascertained cartographic position is transmitted in the form of corresponding items of position information to the processor unit 22.

According to the example, forward-looking sensor devices 68 are attached in the front area 66 of the agricultural tractor 10. These are designed in the form of a stereo camera or a lidar and are used for prior detection of a surface contour 70 of the underlying surface 46 to be driven on. The detected surface contour 70 is provided to the processor unit 22 in the form of corresponding items of contour information.

In addition, the processor unit 22 has access via a CAN data bus 72 to items of information of a drive system 74 and/or an axle load sensor 76 of the agricultural tractor 10.

FIG. 2 shows an exemplary embodiment of the method according to the disclosure illustrated as a block diagram, which is to be explained hereinafter with reference to FIG. 1. A single track drive 16*i* (i=a, . . . , d) is shown here as a representative. To improve the quality of the ascertainment of the soil condition, however, the method according to the disclosure can be carried out incorporating some or all provided track drives 16*a*, . . . , 16*d* of the agricultural tractor 10.

The sequence of the method may be divided into two function blocks. In a first function block 78, when driving on the underlying surface 46, which is assumed to be compressible, a kinematic behavior of the track drive 16*i* caused by sinking is thus observed via the detection device 24, whereupon, in a second function block 80, at least one parameter characterizing the soil condition is concluded by the assessment device 26 or the processor unit 22 comprised thereby starting from the observed kinematic behavior of the track drive 16*i*.

The latter takes place in that the kinematic behavior observed via the detection device 24 is supplied to a prediction model 82 specified for the relevant track drive 16*i*, on the basis of which a statement is in turn made with respect to the soil condition.

The prediction model 82, which is ultimately an algorithm, is trained beforehand on the basis of empirically performed test and measurement series and uploaded into the processor unit 22, more specifically into the associated memory unit 28. The prediction model 82 establishes a clear correlation between the observed kinematic behavior of the track drive 16*i* and the respective soil condition.

According to the example, the kinematic behavior of the track drive 16*i* results due to a deflection, which occurs because of travel on a chassis component of the track drive 16*i* mounted to be movable in relation to the underlying surface 46, more specifically the base part 56, wherein in the present case this results in an angle change α around the pivot joint axis 60 sensorially detected via the incremental rotational encoder 62. A traction torque occurring on the drive belt 38 because of the drive in relation to the underlying surface 46 thus causes asymmetrical sinking of the track drive 16*i* counter to the travel direction 84, which is expressed in a corresponding angle change α (see FIG. 2).

Notwithstanding this, in complex drive arrangements, in addition to the base part 56, further movable chassis components can also be provided, which are used for the spring suspension and/or the tensioning of the drive belt 38 via associated deflection, tensioning, and support rollers 44. A complex and therefore particularly distinctive deflection pattern results from the comprehensive sensorial detection of the movements insofar occurring, which permits an accurate inference of the respective soil condition.

Additionally or alternatively, the kinematic behavior of the track drive 16*i* results due to a normal and/or tangential acceleration, which occurs because of travel on a section 86 of the drive belt 38 facing toward the underlying surface 46. In this case, the knowledge of the normal and/or tangential acceleration is used by the processor unit 22 to ascertain the orientation of the relevant belt section 86 in relation to the underlying surface 46.

The normal and/or tangential acceleration is determined via the first acceleration sensor wherein the radio interface 36 transmits a data stream representing this wirelessly to the second wireless interface 34 and from there to the processor unit 22. The vehicle chassis 50 is used as a reference system for ascertaining the orientation of the belt section 86, for which purpose the processor unit 22 determines an associated reference orientation via the second acceleration sensor 48.

Since the drive belt 38 is deflected multiple times along its course, a number of acceleration measurement modules 52 corresponding to the deflection points 88 is arranged distributed along the drive belt 38 for uninterrupted detection of the normal and/or tangential acceleration. In the present case, a total of three identical acceleration measurement modules 52 are provided. Contrary to the illustration in FIG. 2, the acceleration measurement modules 52 are attached equidistantly along the drive belt 38.

For the most accurate possible ascertainment of the soil condition, it is provided that the observed kinematic behavior of the track drive 16*i* is filtered by the processor unit 22 with respect to soil irregularities 90 located in the travel direction 84. The detection of the soil irregularities 90 is carried out via the forward-looking sensor devices 68.

The parameters characterizing the soil condition are typically items of information with respect to a soil moisture, a soil structure, a soil compaction, and/or a soil type. In the present example, the ascertainment of the soil condition is restricted to a selection of the above-mentioned parameters shown in FIG. 2 (soil structure, soil compaction, and soil type), wherein specifications with respect to a current moisture content, therefore the soil moisture, originate from alternative data sources and thus contribute to improved accuracy of the remaining parameters. The moisture content results, for example, from items of weather information, even better from a soil measurement carried out on location. The results of the soil measurement are uploaded via the first wireless interface 30 into the memory unit 28, so that the processor unit 22 has access thereto.

In order to make the items of information obtained with regard to the soil condition usable in particular when driving on the same field surface again, the ascertained parameters are located by linking to the items of position information provided on the part of the navigation system 64 and transmitted as a data set via the first wireless interface 30 to the central data server 32. From there, these can be downloaded by a user for circuit diagram creation or process optimization.

Since the compression effect caused by the respective track drive 16*i* is also dependent on the extent of the traction torque occurring on the drive belt 38 in relation to the underlying surface 46 because of drive and/or the axle load acting in the linkage point of the track drive 16*i* formed by the pivot joint 58 in relation to the vehicle chassis 50 because of weight, furthermore corresponding items of information of the drive system 74 and/or the axle load sensor 76 are taken into consideration by the processor unit 22 to improve the accuracy of the prediction model 82 via the CAN data bus 72.

For the sake of completeness, it is to be noted that the use of the method according to the disclosure is not restricted to agricultural tractors, rather it may also be used in any other desired work machines or work devices, if they are equipped with a track drive.

The terminology used herein is for the purpose of describing example embodiments or implementations and is not intended to be limiting of the disclosure. As used herein, the singular forms "a," "an," and "the" are intended to include the plural forms as well, unless the context clearly indicates otherwise. It will be further understood that the any use of the terms "has," "includes," "comprises," or the like, in this specification, identifies the presence of stated features, integers, steps, operations, elements, and/or components, but does not preclude the presence or addition of one or more other features, integers, steps, operations, elements, components, and/or groups thereof.

Those having ordinary skill in the art will recognize that terms such as "above," "below," "upward," "downward," "top," "bottom," etc., are used descriptively for the figures, and do not represent limitations on the scope of the present disclosure, as defined by the appended claims. Furthermore, the teachings may be described herein in terms of functional and/or logical block components or various processing steps, which may include any number of hardware, software, and/or firmware components configured to perform the specified functions.

Terms of degree, such as "generally," "substantially," or "approximately" are understood by those having ordinary skill in the art to refer to reasonable ranges outside of a given value or orientation, for example, general tolerances or positional relationships associated with manufacturing, assembly, and use of the described embodiments or implementations.

As used herein, "e.g.," is utilized to non-exhaustively list examples and carries the same meaning as alternative illustrative phrases such as "including," "including, but not limited to," and "including without limitation." Unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

While the above describes example embodiments or implementations of the present disclosure, these descriptions should not be viewed in a restrictive or limiting sense. Rather, there are several variations and modifications which may be made without departing from the scope of the appended claims.

What is claimed is:

1. A method for ascertaining a soil condition, comprising:
    observing via a detection device, including a sensor, a kinematic behavior of a track drive when the track drive sinks into a soil of a surface while driving on the surface, the observed kinematic behavior being associated with a rotation of a chassis component of the track drive about a pivot joint, and the chassis component being mounted such that it is rotatable about the pivot joint while driving on the surface; and
    determining via an assessment device, including a processor connected to a memory, at least one parameter characterizing a soil condition based in part on the observed kinematic behavior of the track drive.

2. The method of claim 1, wherein the observed kinematic behavior is associated with a normal or tangential acceleration of a drive belt of the track drive facing the surface, the normal or tangential acceleration is determined via an acceleration sensor module being a part of the detection device, the acceleration sensor module includes an acceleration sensor, the acceleration sensor module is embedded in the drive belt, and a data stream representing the normal or tangential acceleration is transmitted wirelessly from the acceleration sensor module to the assessment device.

3. The method of claim 2, wherein the drive belt is deflected a plurality of times along its course, and a plurality of acceleration sensor modules, corresponding to a plurality deflection points of the drive belt, are arranged in a distributed manner along the drive belt.

4. The method of claim 1, wherein the observed kinematic behavior of the track drive is filtered by the assessment device with respect to irregularities of the surface located in a travel direction of the track drive on the surface.

5. The method of claim 1, wherein the at least one parameter characterizing the soil condition includes one or more of the following: a soil moisture, a soil structure, a soil compaction, and a soil type.

6. The method of claim 1, wherein a location of the at least one parameter is located via a navigation system communicating with the assessment device by linking a position ascertained by the navigation system to an associated cartographic position and transmitting, as a data set, the location of the at least one parameter to a central data server.

7. The method of claim 1, wherein the sensor of the detection device includes a rotational encoder.

8. A method for ascertaining a soil condition, comprising:
    observing via a detection device, including a sensor, a kinematic behavior of a track drive when the track drive sinks into a soil of a surface while driving on the surface, the observed kinematic behavior of the track drive being filtered by the assessment device with respect to irregularities of the surface located in a travel direction of the track drive on the surface; and
    determining via an assessment device, including a processor connected to a memory, at least one parameter characterizing a soil condition based in part on the observed kinematic behavior of the track drive.

9. The method of claim 8, wherein the observed kinematic behavior is associated with a normal or tangential acceleration of a drive belt of the track drive facing the surface, the normal or tangential acceleration is determined via an acceleration sensor module being a part of the detection device, the acceleration sensor module includes an acceleration sensor, the acceleration sensor module is embedded in the drive belt, and a data stream representing the normal or tangential acceleration is transmitted wirelessly from the acceleration sensor module to the assessment device.

10. The method of claim 9, wherein the drive belt is deflected a plurality of times along its course, and a plurality of acceleration sensor modules, corresponding to a plurality deflection points of the drive belt, are arranged in a distributed manner along the drive belt.

11. The method of claim 8, wherein the at least one parameter characterizing the soil condition includes one or more of the following: a soil moisture, a soil structure, a soil compaction, and a soil type.

12. The method of claim 8, wherein a location of the at least one parameter is located via a navigation system communicating with the assessment device by linking a position ascertained by the navigation system to an associated cartographic position and transmitting, as a data set, the location of the at least one parameter to a central data server.

13. The method of claim 8, wherein the sensor of the detection device includes a rotational encoder.

14. A system for ascertaining a soil condition, comprising:
a detection device, including a sensor, configured to observe a kinematic behavior of a track drive when the track drive sinks into a soil of a surface while driving on the surface, the observed kinematic behavior being associated with a rotation of a chassis component of the track drive about a pivot joint, and the chassis component being mounted such that it is rotatable about the pivot joint while driving on the surface; and
an assessment device, including a processor connected to a memory, configured to determine at least one parameter characterizing a soil condition based in part on the observed kinematic behavior of the track drive, the soil condition including one or more of the following: a soil moisture, a soil structure, a soil compaction, and a soil type.

15. The system of claim 14, wherein the observed kinematic behavior is associated with a normal or tangential acceleration of a drive belt of the track drive facing the surface, the normal or tangential acceleration is determined via an acceleration sensor module being a part of the detection device, the acceleration sensor module includes an acceleration sensor, the acceleration sensor module is embedded in the drive belt, and a data stream representing the normal or tangential acceleration is transmitted wirelessly from the acceleration sensor module to the assessment device.

16. The system of claim 15, wherein the drive belt is deflected a plurality of times along its course, and a plurality of acceleration sensor modules, corresponding to a plurality deflection points of the drive belt, are arranged in a distributed manner along the drive belt.

17. The system of claim 16, wherein the observed kinematic behavior of the track drive is filtered by the assessment device with respect to irregularities of the surface located in a travel direction of the track drive on the surface.

18. The system of claim 14, wherein the at least one parameter characterizing the soil condition includes one or more of the following: a soil moisture, a soil structure, a soil compaction, and a soil type.

19. The system of claim 14, wherein a location of the at least one parameter is located via a navigation system communicating with the assessment device by linking a position ascertained by the navigation system to an associated cartographic position and transmitting, as a data set, the location of the at least one parameter to a central data server.

20. The system of claim 14, wherein the sensor of the detection device includes a rotational encoder.

* * * * *